US00PP18923P2

(12) United States Plant Patent
Freyre

(10) Patent No.: US PP18,923 P2
(45) Date of Patent: Jun. 10, 2008

(54) ***BROWALLIA* HYBRIDA NAMED 'UNHBR4'**

(50) Latin Name: *Browallia speciosa*
Varietal Denomination: UNHBR 4

(75) Inventor: Rosanna Freyre, Gainsville, FL (US)

(73) Assignee: University of New Hampshire, Durham, NH (US)

( * ) Notice: Subject to any disclaimer, the term of this patent is extended or adjusted under 35 U.S.C. 154(b) by 0 days.

(21) Appl. No.: 11/656,760

(22) Filed: Jan. 23, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Annette H Para
(74) *Attorney, Agent, or Firm*—Devine, Millimet, Branch; Paul C. Remus

(57) ABSTRACT

A new and distinct cultivar of *Browallia* plant named 'UNHBR4', characterized by numerous single flowers that are purple pink in color with a small white center, compact and rounded plant growth, stems that do not break or separate on the center of the mature plant, and good performance in partial shade in the garden and as a hanging basket.

2 Drawing Sheets

GOVERNMENT SPONSORSHIP

The present invention uwas funded in part by the USDA/Cooperative State Research, Education and Extension Service, of the United States Government Under Contract No. 01-90015-0420.

Botanical classification/cultivar designation: *Browallia* hybrida named 'UNHBR4'.

BACKGROUND OF THE INVENTION

The present Invention relates to a new and distinct cultivar of *Browallia* plant, botanically known as a *Browallia speciosa,* and hereinafter referred to by the cultivar name 'UNHBR4'.

The new *Browallia* is a product of a planned breeding program conducted by the Inventor in Durham. N.H. The objective of the breeding program is to create new compact *Browallia* plants with attractive flowers in a range of colors, profuse flowering and reduced fruit set.

The new 'UNHBR4' originated from a manual self pollination made by the Inventor on Dec. 4, 2001 on proprietary selection UNH B010-13 resulting from hybridization between a proprietary selection of *Browallia speciosa* code BROW7, not patented, used as female, and a proprietary selection of *Browallia speciosa* BROW5-1, not patented, used as male. Seed was sown on Feb. 14, 2002. From the segregating progeny, a single plant BR2-10-1, later coded as 'UNHBR4' was selected in Durham, N.H., USA, on the basis of its profuse flowering, compact growth habit and attractive flowers.

Asexual reproduction of the new cultivar by terminal vegetative cuttings since June 2002 in Durham, N.H. has shown that the unique features of this new *Browallia* are stable and reproduced true to type in successive generations.

SUMMARY OF THE INVENTION

Plants of the cultivar 'UNHBR4' have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'UNHBR4'. These characteristics in combination distinguish 'UNHBR4' as a new and distinct cultivar:

1. Numerous single flowers that are purple pink in color with a small white center.
2. Compact and rounded plant growth habit.
3. Stems do not break or separate on the center of the mature plant.
4. Good performance in partial shade in the garden and as a hanging basket.

Of the *Browallia* cultivars known to the inventor, 'UNHBR4' differs primarily by its unique purple pink flower color.

BRIEF DESCRIPTION OF THE PHOTOGRAPHS

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Browallia.*

One photograph comprises a side perspective view of one typical five-month 20-cm container of 'UNHBR4' with three plants.

A second photograph is a close-up view of typical flowers and leaves of 'UNHBR4'.

DETAILED BOTANICAL DESCRIPTION

The aforementioned photographs and following observations and measurements describe plants grown in Durham, N.H., in a heated greenhouse with 21° C. day/18° C. night set points. After planting rooted cuttings, plants were grown for about three months in 20-cm containers with three plants per container. Color references are made to The Royal Horticultural Society Colour Chart, 1995 Edition, except where general terms of ordinary dictionary significance are used. Color was evaluated under indirect, natural light.

Botanical classification: *Browallia speciosa* cultivar 'UNHBR4'.

Parentage:

*Female parent.*—Proprietary selection of *Browallia speciosa* code UNHBR4 B010-13, not patented.

*Male parent.*—Proprietary selection of *Browallia speciosa* code UNHBR4 B010-13, not patented.

Propagation:

*Type cutting.*—Terminal vegetative cuttings.

*Time to initiate roots.*—About seven days at 21° C.

*Time to develop roots.*—About 15 days at 21° C.

*Root description.*—Fine, fibrous; white, color 155D.

*Rooting habit.*—Freely branching.

Plant description:

*Form.*—Annual flowering plant; moderately vigorous; compact plant habit; uniformly mounded plant form. Freely branching habit with lateral branches potentially forming at very node. Continuous flowering, day neutral.

*Plant height.*—About 24 cm.

*Plant diameter* (*area of spread*), *single plant.*—About 50 cm.

*Vigor.*—Moderately vigorous.

*Lateral branches.*—Length: 15 cm. Diameter: About 2 mm. Internode length: 2.8 cm. Texture: glabrous. Color: 143B.

*Foliage description.*—Arrangement: Alternate. Length: About 4 cm. Width: 1.5 cm. Shape: Lanceolate to elliptic. Apex: Acute. Base: Rounded. Margin: Ciliolate. Texture: Mostly glabrous but has very sparse minute hairs on the upper surface, the lower surface has hairs on the midrib and secondary veins. Venation pattern: Pinnate. Color: Developing leaves, upper and lower surfaces: 143B. Fully expanded leaves, upper surface: 137A. Fully expanded leaves, lower surface: 144A. Venation, upper and lower surfaces: 144A.

Flower description:

*Flower type and habit.*—Salverform; single, axillary. Flowers face outward at foliage level. Flowers not fragrant. Very freely flowering, typically about three open flowers and three flower buds per lateral branch at one time.

*Natural flowering season.*—Plants flower from April to October in the Northern Hemisphere until frost in the autumn; flowering continuous during this period. Plants will flower under short or long days in a greenhouse.

*Flower longevity on the plant.*—About seven days.

*Fragrance.*—None detected.

*Flower size.*—Diameter: 3.8-4.8 cm. Depth (height from base of the calyx): 3-3.5 cm.

*Flower buds* (*showing color*).—Length: About 1.5 cm. Diameter: 4 mm. Shape: Oblong. Color: 144B.

*Petals.*—Quantity/arrangement: Salverform corolla, five petal lobes fused in a star shape. Occasionally six lobes. Petal length: About 1.5-2 cm. Petal width: About 1.2-2.2 cm. Shape: Star. Apex: Rounded. Base: Fused. Margin: Entire. Texture, upper and lower surfaces: Smooth, with longitudinal venation. Color: When opening, upper surface: 87A. When opening, lower surface: 85B. Fully opened, upper surface: 87B; upper center: 155C. Fully opened, lower surface: 85D; lower center: 145B.

*Sepals.*—Arrangement/appearance: Five sepals. Length: About 7 mm. Width: About 1-2 mm. Shape: ovate. Apex: Acute. Base: Fused. Margin: Ciliolate. Texture, upper and lower surfaces: Sparsely covered with minute hairs. Color, upper and lower surfaces: 144B. Total length of calyx: About 1.5 cm.

*Pedicels.*—Length: About 1.8 cm. Width: About 1 mm. Angle: About 45° from the main stem. Strength: Moderately strong. Texture: Covered with very minute hairs. Color: 152A.

*Reproductive organs.*—Stamens: Quantity per flower: Four, 2 long and 2 short. Filaments on the long stamens are folded over, visible in the center of the corolla, and are covered with a purple fuzz. Anther shape: Kidney, with two theca. Anther length: About 1 mm. Anther width: About 0.8 mm. Anther color: 22A. Pollen amount: Abundant. Pollen color: 4C. Pistils: Quantity per flower: One. Pistil length: About 2 cm. Style length: About 1.8 cm. Style color: 145C. Stigma shape: Oval. Stigma color: 144A. Ovary color: 144A.

*Seed/fruit.*—Seed and/or fruit production is moderate under open pollination with other *Browallia* plants. About 60% fruit set observed from manual self-pollination.

Disease/pest resistance: Plants of the new *Browallia* have not been noted to be resistant to pathogens or pests common to *Browallia*.

Garden performance: 'UNHBR4' has good tolerance to drought conditions and will recover well from wilt. Better growth and flowering is seen under part-shade conditions. Flowers tend to fade under full sun.

What is claimed is:

1. A new and distinct cultivar of *Browallia* plant named 'UNHBR4' as illustrated and described.

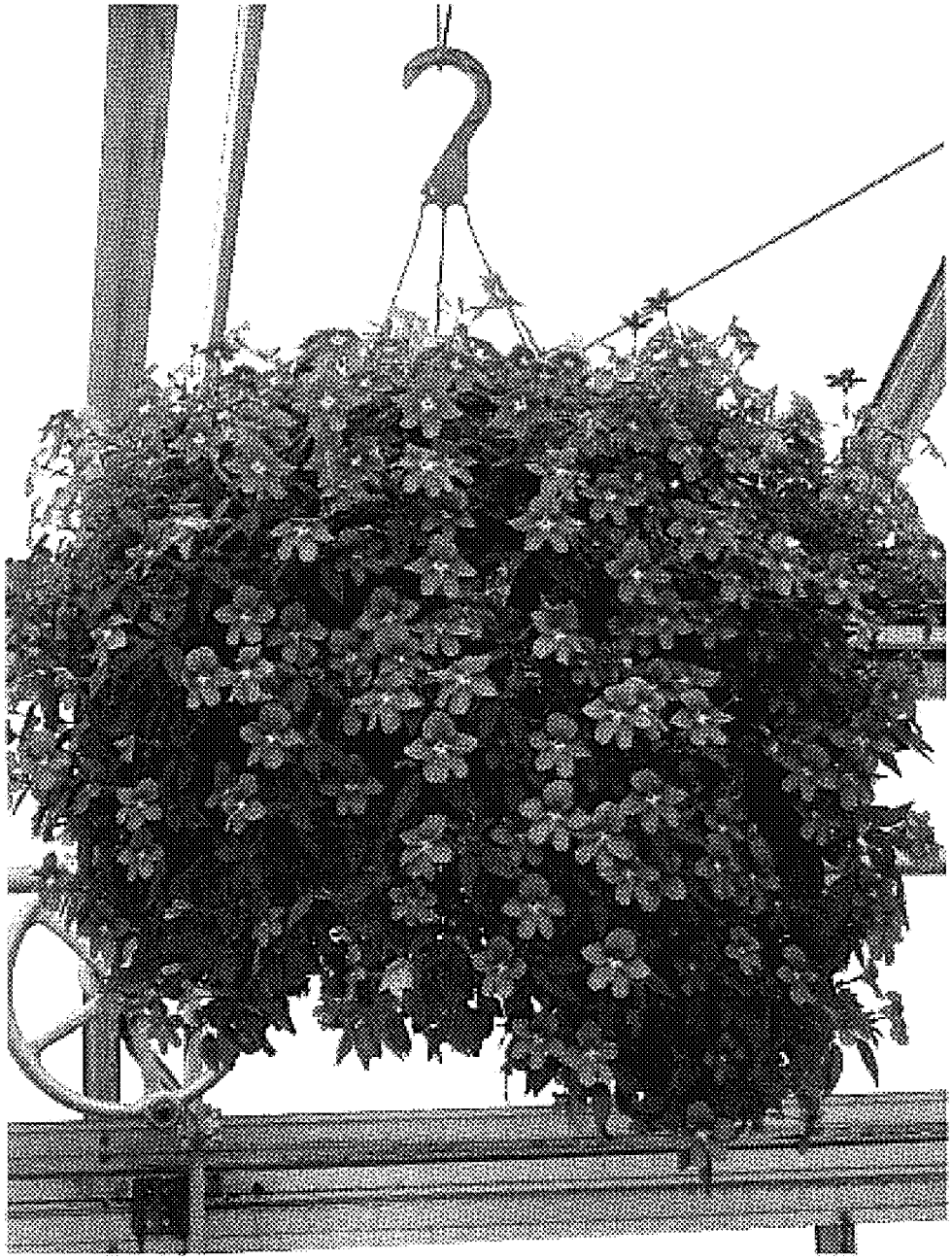

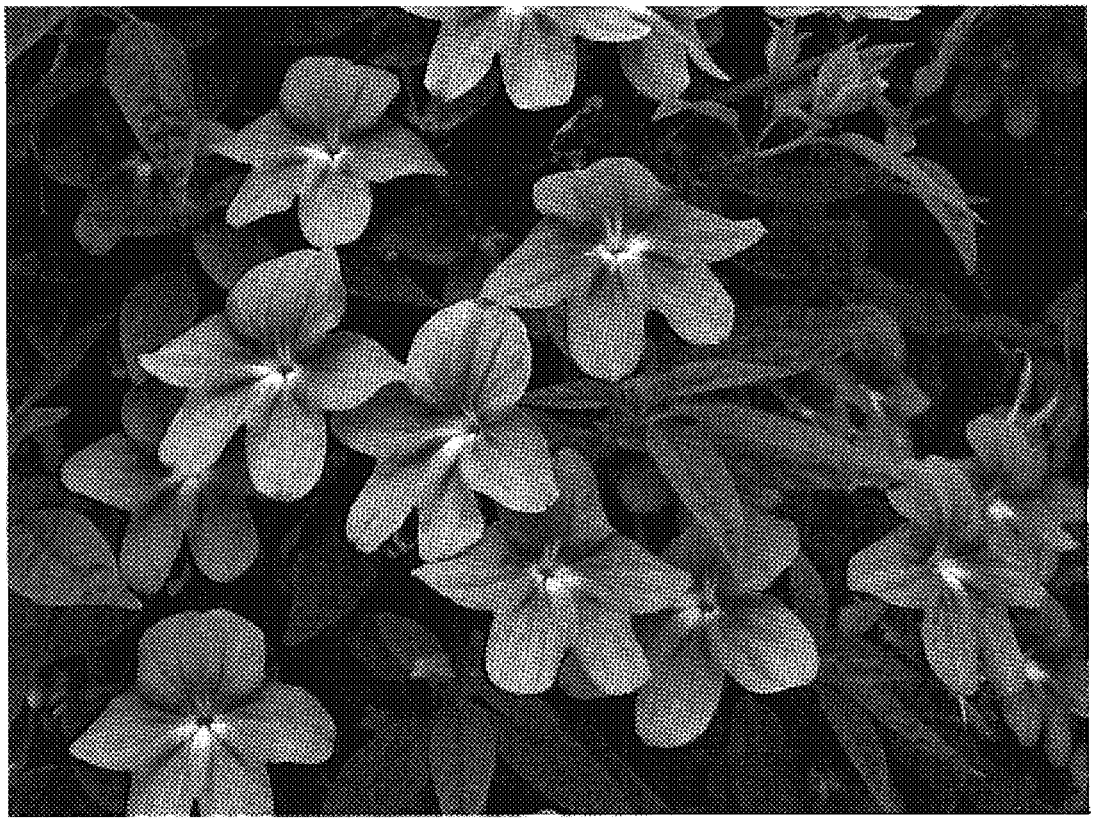

* * * * *